United States Patent
Mahendrakar

(10) Patent No.: US 12,311,877 B2
(45) Date of Patent: May 27, 2025

(54) KEY DEVICE FOR OPENING AT LEAST ONE DOOR OF A MOTOR VEHICLE

(71) Applicant: MERCEDES-BENZ GROUP AG, Stuttgart (DE)

(72) Inventor: Pramod Mahendrakar, Bengaluru (IN)

(73) Assignee: MERCEDES-BENZ GROUP AG, Stuttgart (DE)

( * ) Notice: Subject to any disclaimer, the term of this patent is extended or adjusted under 35 U.S.C. 154(b) by 114 days.

(21) Appl. No.: 18/039,010

(22) PCT Filed: Nov. 8, 2021

(86) PCT No.: PCT/EP2021/080917
§ 371 (c)(1),
(2) Date: May 26, 2023

(87) PCT Pub. No.: WO2022/111981
PCT Pub. Date: Jun. 2, 2022

(65) Prior Publication Data
US 2024/0001887 A1 Jan. 4, 2024

(30) Foreign Application Priority Data

Nov. 30, 2020 (GB) ...................................... 2018802

(51) Int. Cl.
| | |
|---|---|
| B60R 25/24 | (2013.01) |
| A61L 2/18 | (2006.01) |
| A61L 2/26 | (2006.01) |
| B05B 11/04 | (2006.01) |

(52) U.S. Cl.
CPC ................ *B60R 25/24* (2013.01); *A61L 2/18* (2013.01); *A61L 2/26* (2013.01); *B05B 11/048* (2013.01); *A61L 2202/15* (2013.01)

(58) Field of Classification Search
CPC ... B60R 25/24; A61L 2/18; A61L 2/26; A61L 2202/15; B05B 11/048; E05B 19/00; A47K 5/1201
See application file for complete search history.

(56) References Cited

U.S. PATENT DOCUMENTS

| | | | |
|---|---|---|---|
| 3,086,384 A | 4/1963 | Wyche | |
| 4,925,066 A * | 5/1990 | Rosenbaum | ........ B05B 11/0037 222/129 |

(Continued)

FOREIGN PATENT DOCUMENTS

| | | |
|---|---|---|
| DE | 7640210 U1 | 4/1977 |
| DE | 3148891 A1 | 11/1982 |

(Continued)

OTHER PUBLICATIONS

Office Action dated Sep. 3, 2024 in related/corresponding JP Application No. 2023-532587.

(Continued)

*Primary Examiner* — Omeed Alizada
(74) *Attorney, Agent, or Firm* — PATENT PORTFOLIO BUILDERS PLLC

(57) ABSTRACT

A key device for opening at least one door of a motor vehicle includes a housing. At least one opening mechanism for opening the at least one door is arranged on the housing. A reservoir for storing a liquid is arranged on an outer side of the housing. The reservoir is configured to store a disinfection fluid in an interior of the reservoir. The reservoir includes a push mechanism and a nozzle for spraying the disinfection fluid from the interior into the surroundings of the key device after the push mechanism is pushed by a user of the key device.

10 Claims, 2 Drawing Sheets

(56) References Cited

U.S. PATENT DOCUMENTS

| | | | |
|---|---|---|---|
| 5,305,874 A | 4/1994 | McLaughlin | |
| 2006/0032868 A1* | 2/2006 | Grant | B65D 83/205 |
| | | | 222/192 |
| 2007/0264138 A1* | 11/2007 | Mandell | B05B 7/32 |
| | | | 417/382 |
| 2008/0072639 A1* | 3/2008 | Kurdziel | A45F 5/00 |
| | | | 224/272 |

FOREIGN PATENT DOCUMENTS

| | | |
|---|---|---|
| DE | 20005401 U1 | 12/2000 |
| DE | 20205325 U1 | 6/2002 |
| DE | 202020004367 U1 | 10/2020 |
| JP | 2019173382 A | 10/2019 |
| WO | 2006018726 A1 | 2/2006 |

OTHER PUBLICATIONS

Office Action dated Apr. 23, 2024 in related/corresponding JP Application No. 2023-532587.
Office Action dated Jul. 1, 2024 in related/corresponding GB Application No. 2018802.5.
International Search Report and Written Opinion mailed Feb. 1, 2022 in related/corresponding International Application No. PCT/EP2021/080917.
Search Report dated May 27, 2021 in related/corresponding GB Application No. 2018802.5.

* cited by examiner

KEY DEVICE FOR OPENING AT LEAST ONE DOOR OF A MOTOR VEHICLE

FIELD OF THE INVENTION

Exemplary embodiments of the invention relate to the field of automobiles, and more specifically to a key device for opening at least one door of a motor vehicle.

BACKGROUND INFORMATION

In a motor vehicle a user of the motor vehicle touches or contacts a plurality of areas inside and/or outside the motor vehicle with his hands. For example, a user may touch a door handle, a steering wheel, a starting button, or a door opener. It is not predictable, which areas will be touched by the user, which is problematic in view of the risk of germs or viruses possibly infecting this person.

DE 7640210 U1 discloses a car key fob, wherein that fob consists of a container provided with a closable spray nozzle or spray head.

There is a need in the art to provide a key device for a reliable disinfection of a user of the key device.

SUMMARY OF THE INVENTION

Exemplary embodiments of the invention are directed to a key device for a motor vehicle, by which an infection risk for the user of the key device is minimized.

One aspect of the invention relates to a key device for opening at least one door of a motor vehicle, wherein the key device comprises at least one housing, wherein at least one opening mechanism for opening the at least one door is arranged on the housing, and wherein a reservoir for storing a liquid is arranged on an outer side of the housing.

In an embodiment, the reservoir is configured to store a disinfection fluid in an interior of the reservoir, wherein the reservoir comprises a push mechanism and the reservoir comprises a nozzle for spraying the disinfection fluid from the interior of the reservoir into surroundings of the key device after the push mechanism is pushed by a user of the key device.

Therefore, a key device is disclosed, by which an infection risk of the user is minimized. In other words, a sanitizer mechanism is provided in the key device, which allows a user whenever the user wants to ride or drive the motor vehicle to use the disinfection fluid and also to spray the touchable areas with disinfection fluid so that the user is protected against germs and viruses. A corresponding arrangement is provided on the key device for this purpose. This arrangement comprises the disinfection fluid like a pocket sanitizer, wherein the key device may be used anywhere by the user.

The key device according to an embodiment of the present invention has the advantage that the user is protected against germs and viruses. This means that the key device is a health and safety feature.

In an embodiment, the push mechanism comprises a pressing part for the user of the key device to compress the reservoir by pressing a predetermined portion, wherein the pressing part comprises at least one flexible wall for pressing the pressing part. Therefore, the reservoir is fluidically separated from the push mechanism, whereby a leaking of the disinfection fluid from the reservoir is minimized.

In another embodiment, the reservoir comprises a level indicator for indicating a level of the disinfection fluid contained in the interior of the reservoir to a user on an outer wall of the reservoir. The user of the key device can visually perceive the level of the disinfection fluid contained in the interior of the reservoir. Therefore, it is possible that the user may refill the reservoir. In particular, the level indicator is an optical level indicator. In particular, the level indicator indicates if the reservoir is full, to which extent it is filled, or if the reservoir is empty.

According to another embodiment, the reservoir comprises a refill opening for refilling the reservoir with a disinfection fluid from outside the reservoir. Therefore, the key device is very flexibly usable and, if the disinfection fluid reservoir is empty, the user can easily refill the reservoir.

In another embodiment, the pressing part is fluidically separated from the interior of the reservoir. This embodiment has the advantage that a leakage of the key device is minimized.

According to another embodiment, the reservoir comprises a pipe, which is fluidically connected with the pressing part. Therefore, after the pressing part is pressed by a user, the disinfection fluid is passed from the reservoir to the pressing part and/or to the nozzle.

In another embodiment, the reservoir comprises a ball inside the pipe and/or the reservoir comprises a sealing element for sealing the pipe. According to this embodiment, a leakage is avoided.

In a still further embodiment, the pipe comprises a spring for supporting a pressing operation performed by the user and for compressing the pipe. According to this embodiment, when the pressing part is pressed, the pipe is compressed with the aid of the spring, and the disinfection fluid is sprayed through the nozzle.

According to another embodiment the nozzle is configured as a sprinkler element. Therefore, the disinfection fluid may be advantageously distributed through the sprinkler, whereby a hand of the user or an element of the motor vehicle can be efficiently disinfected.

In another embodiment, the opening mechanism is configured for wirelessly opening the at least one door of the motor vehicle. Therefore, the user does not need to touch an opening mechanism at the door of the motor vehicle, whereby the risk of an infection of the user by germs or viruses possibly present on the opening mechanism is minimized.

Further advantages, features, and details of the invention derive from the following description of preferred embodiments as well as from the accompanying drawings. The features and feature combinations previously mentioned in the description as well as the features and feature combinations mentioned in the following description of the figures and/or shown in the figures alone can be employed not only in the respectively indicated combination but also in any other combination or taken alone without leaving the scope of the invention.

BRIEF DESCRIPTION OF THE DRAWINGS

The novel features and characteristics of the disclosure are set forth in the independent claims. The accompanying drawings, which are incorporated in and constitute part of this disclosure, illustrate exemplary embodiments and together with the description, serve to explain the disclosed principles. In the figures, the same reference signs are used throughout the figures to refer to identical features and components. Some embodiments of the system and/or methods in accordance with embodiments of the present subject-matter are now described below, by way of example only, and with reference to the accompanying figures.

The drawings show in.

In the figures the same elements or elements having the same function are indicated by the same reference signs.

DETAILED DESCRIPTION

Figure 1:
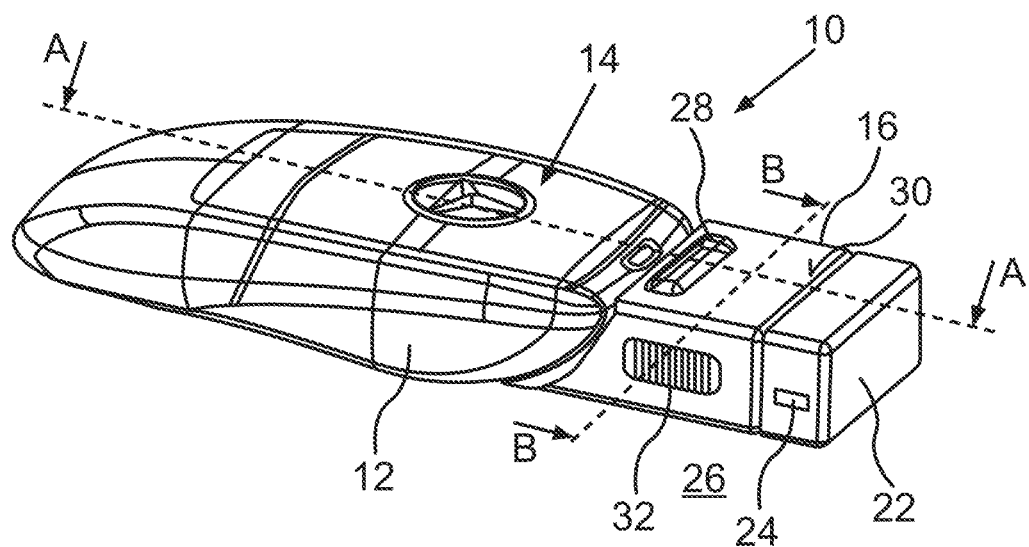
FIG. 1 a perspective view of an embodiment of a key device.

In the present document, the word "exemplary" is used herein to mean "serving as an example, instance, or illustration." Any embodiment or implementation of the present subject matter described herein as "exemplary" is not necessarily to be construed as preferred or advantageous over other embodiments.

While the disclosure is susceptible to various modifications and alternative forms, specific embodiments thereof have been shown by way of example in the drawings and will be described in detail below. It should be understood, however, that it is not intended to limit the disclosure to the particular forms disclosed, but on the contrary, the disclosure is to cover all modifications, equivalents, and alternatives falling within the scope of the disclosure.

The terms "comprises", "comprising", or any other variations thereof, are intended to cover a non-exclusive inclusion so that a setup, device or method that comprises a list of components or steps does not include only those components or steps but may include other components or steps not expressly listed or inherent to such setup or device or method. In other words, one or more elements in a system or apparatus preceded by "comprises" or "comprise" does not or do not, without more constraints, preclude the existence of other elements or additional elements in the system or method.

In the following detailed description of the embodiments of the disclosure, reference is made to the accompanying drawings that form part hereof, and in which are shown by way of illustration specific embodiments in which the disclosure may be practiced. These embodiments are described in sufficient detail to enable those skilled in the art to practice the disclosure, and it is to be understood that other embodiments may be utilized and that changes may be made without departing from the scope of the present disclosure. The following description is, therefore, not to be taken in a limiting sense.

FIG. 1 shows a perspective view of an embodiment of a key device 10. The key device 10 is configured for opening at least one door of a motor vehicle. The key device 10 comprises at least one housing 12, wherein at least one opening mechanism 14 for opening the at least one door is arranged at the housing 12. The key device 10 comprises a reservoir 16 for storing a liquid or fluid, wherein the reservoir 16 is arranged on an outer side of the housing 12.

In an embodiment, the reservoir 16 is configured to store a disinfection fluid 18 (see FIG. 2) in an interior 20 (see FIG. 2) of the reservoir 16, wherein the reservoir 16 comprises a push mechanism 22 and the reservoir 16 comprises a nozzle 24 for spraying the disinfection fluid 18 from the interior 20 into the surroundings 26 of the key device 12 after the push mechanism 22 is pushed by a user of the key device 10.

According to the embodiment shown in FIG. 1, the key device 10 comprises the reservoir 16 containing the disinfection fluid 18, wherein the reservoir 16 is integrated in the key device 10.

The push mechanism 22 may also be regarded as a top cap of the reservoir 16. Furthermore, FIG. 1 shows a first sectional view A-A and a second sectional view B-B, which are shown in more detail in FIG. 2 and FIG. 3.

According to the embodiment shown in FIG. 1, the reservoir 16 comprises a level indicator 28 for indicating a level of the disinfection fluid 18 presently contained in the interior 20 to the user on an outer wall 30 of the reservoir 16. Furthermore, the shown embodiment of the reservoir 16 comprises a refill opening 32 for refilling the reservoir 16 with the disinfection fluid 18 from outside, in particular from the surroundings 26 of the reservoir 16.

Figure 2:
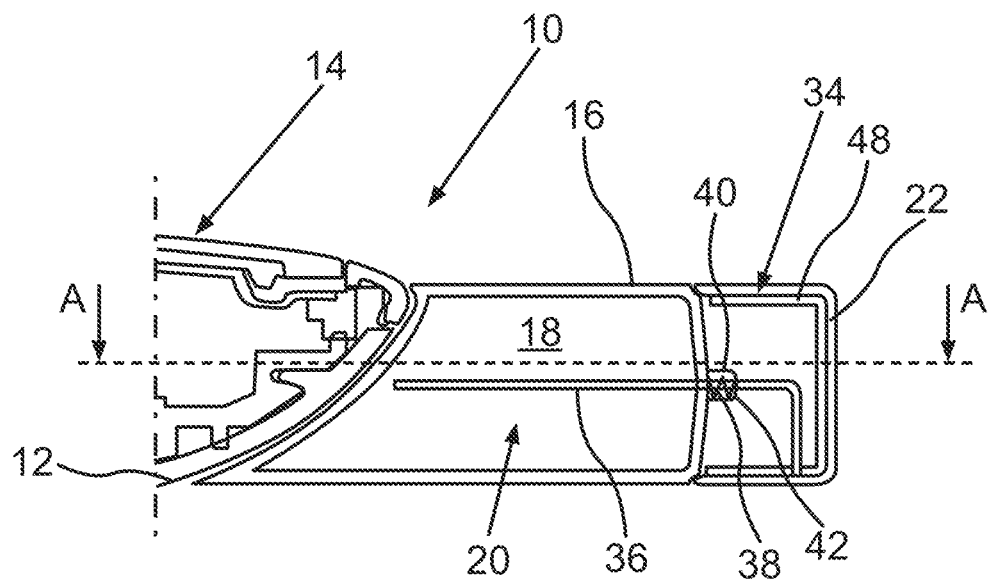
FIG. 2 a schematic sectional view according to the embodiment shown in FIG. 1.

FIG. 2 shows a sectional view of the key device 10 according to FIG. 1 in the section A-A. The embodiment according to FIG. 2 shows that the push mechanism 22 comprises a pressing part 34 for the user of the key device 10 to compress the reservoir 16 at a predetermined portion, wherein the pressing part 34 comprises at least one flexible wall 48 for pressing the pressing part 34. According to the embodiment, the pressing part 34 is fluidically separated from the interior 20 of the reservoir 16. Furthermore, the reservoir 16 may comprise a pipe 36, which is fluidically connected with the pressing part 36. The reservoir 16 according to the shown embodiment comprises a ball 38 inside the pipe 36 and/or the reservoir 16 comprises a sealing element 40 for sealing the pipe 36. Furthermore, the pipe 36 may comprise a spring 42 for supporting a pressing operation performed by the user and for compressing the pipe 36.

The nozzle 24 may be configured as a sprinkler element. Furthermore, the opening mechanism 14 is configured for wirelessly opening the at least one door of the motor vehicle.

FIG. 2 shows that in this embodiment the reservoir 16 is integrated in the key device 10. The reservoir 16 comprises a top cap, which may be the pressing part 34, wherein when the pressing part 34 is pressed by the user, the pipe 36 will be compressed with the aid of the spring 42, and the disinfection fluid 18 exits through the sprinkler. To avoid leakages, the sealing element 40, which may be in particular a rubber sealing element, is provided inside the spring 42, and the ball 40 is provided inside the pipe 36.

Figure 3:
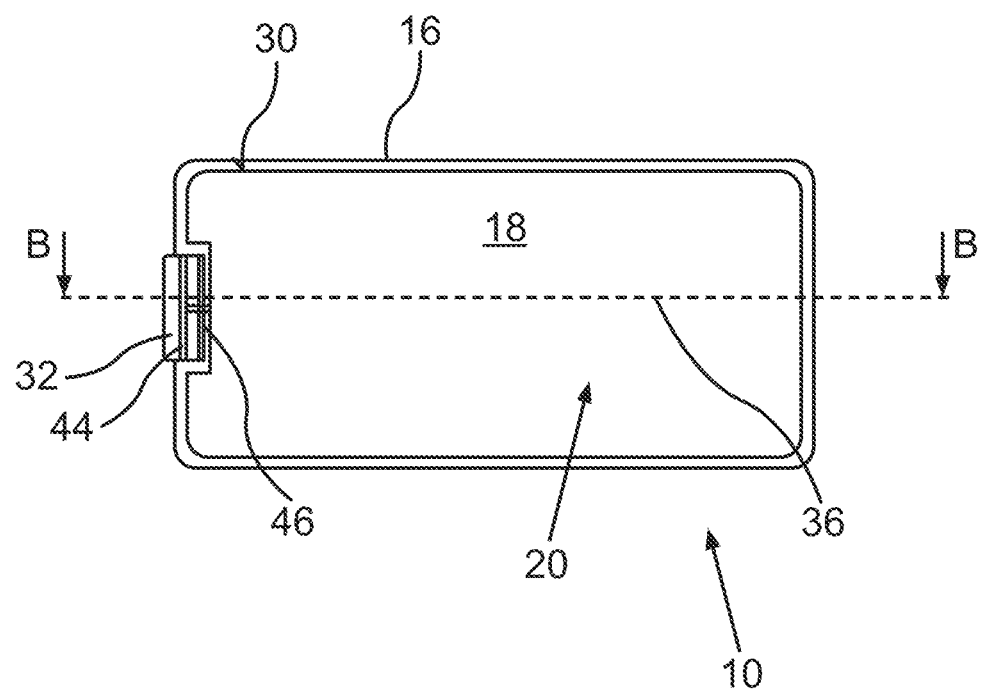
FIG. 3 another schematic sectional view according to the embodiment shown in FIG. 1.

FIG. 3 shows another embodiment of the key device 10 according to the section B-B of FIG. 1. FIG. 3 shows that the refill opening 32 may also comprise a rubber gasket 44 and a refill hole 46. The refill opening 32 may be provided to refill the disinfection fluid 18 through the refill hole 46 when the reservoir 18 is empty. The refill opening 32 may comprise the rubber gasket 44 and/or a rubber cap to avoid leakage.

The embodiments show an automotive vehicle master key comprising a pocket sanitizer.

The invention claimed is:

1. A key device for opening at least one door of a motor vehicle, wherein the key device comprises:
    at least one housing having a housing wall;
    at least one opening mechanism for opening the at least one door arranged at the housing; and
    a reservoir for storing a liquid is arranged on an outer side of the housing wall,
    wherein the reservoir
        is configured to store a disinfection fluid in an interior of the reservoir, comprises a push mechanism, and comprises a nozzle configured to spray the disinfection fluid from the interior of the reservoir into surroundings of the key device after the push mechanism is pushed by a user of the key device,
wherein a portion of the reservoir storing the disinfection fluid is interposed between the outer side of the housing wall and the push mechanism.

2. The key device of claim 1, wherein the push mechanism comprises a pressing part configured for the user of the key device to compress the reservoir at a predetermined portion of the key device, wherein the pressing part comprises at least one flexible wall for pressing the pressing part.

3. The key device of claim 1, wherein the reservoir comprises a level indicator indicating a level of the disinfection fluid contained in the interior to the user on an outer wall of the reservoir.

4. The key device of claim 1, wherein the reservoir comprises a refill opening configured to refill the reservoir with the disinfection fluid from outside the reservoir.

5. The key device of claim 2, wherein the pressing part is fluidically separated from the interior of the reservoir.

6. The key device of claim 5, wherein the reservoir comprises a pipe fluidically connected with the pressing part.

7. The key device of claim 6, wherein
the reservoir comprises a ball inside the pipe, or
the reservoir comprises a sealing element for sealing the pipe.

8. The key device of claim 6, wherein the pipe comprises a spring configured to support a pressing operation performed by the user and configured to compress the pipe.

9. The key device of claim 1, wherein the nozzle is configured as a sprinkler element.

10. The key device of claim 1, wherein the opening mechanism is configured to wirelessly open the at least one door of the motor vehicle.

* * * * *